(12) United States Patent
Nabi et al.

(10) Patent No.: US 12,133,908 B2
(45) Date of Patent: Nov. 5, 2024

(54) PERSONAL CARE COMPOSITION COMPRISING TAURINE, ARGININE, GLYCINE

(71) Applicant: Colgate-Palmolive Company, New York, NY (US)

(72) Inventors: Zeenat Nabi, Cranbury, NJ (US); Shujiang Cheng, Warren, NJ (US); Halyna Siomyk, Cliffside Park, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/877,821

(22) Filed: May 19, 2020

(65) Prior Publication Data

US 2020/0276098 A1   Sep. 3, 2020

Related U.S. Application Data

(62) Division of application No. 16/066,896, filed as application No. PCT/US2015/068279 on Dec. 31, 2015, now Pat. No. 11,026,873.

(51) Int. Cl.

| | | |
|---|---|---|
| A61K 31/198 | (2006.01) |
| A61K 8/02 | (2006.01) |
| A61K 8/04 | (2006.01) |
| A61K 8/44 | (2006.01) |
| A61K 8/46 | (2006.01) |
| A61K 31/185 | (2006.01) |
| A61Q 5/02 | (2006.01) |
| A61Q 5/12 | (2006.01) |
| A61Q 15/00 | (2006.01) |
| A61Q 17/00 | (2006.01) |
| A61Q 19/00 | (2006.01) |
| A61Q 19/10 | (2006.01) |

(52) U.S. Cl.
CPC ............. *A61K 8/44* (2013.01); *A61K 8/0216* (2013.01); *A61K 8/042* (2013.01); *A61K 8/463* (2013.01); *A61K 8/466* (2013.01); *A61K 31/185* (2013.01); *A61K 31/198* (2013.01); *A61Q 5/02* (2013.01); *A61Q 5/12* (2013.01); *A61Q 15/00* (2013.01); *A61Q 17/00* (2013.01); *A61Q 19/00* (2013.01); *A61Q 19/007* (2013.01); *A61Q 19/10* (2013.01); *A61K 2800/28* (2013.01)

(58) Field of Classification Search
CPC ........ A61Q 19/10; A61Q 19/00; A61Q 15/00; A61Q 5/12; A61Q 5/02; A61Q 17/00; A61Q 19/007; A61K 8/44; A61K 31/198
See application file for complete search history.

(56) References Cited

U.S. PATENT DOCUMENTS

| | | |
|---|---|---|
| 8,765,794 B2 | 7/2014 | McCord |
| 10,780,042 B2 | 9/2020 | Krutmann et al. |
| 10,864,147 B2 | 12/2020 | Hilliard, Jr. et al. |
| 11,039,993 B2 | 6/2021 | Maron et al. |
| 2003/0133961 A1 | 7/2003 | Nakamura |
| 2005/0238679 A1 | 10/2005 | Biergiesser et al. |
| 2006/0127342 A1 | 6/2006 | Levis |
| 2006/0165636 A1 | 7/2006 | Hasebe et al. |
| 2012/0058057 A1 | 3/2012 | Pitner et al. |
| 2012/0114583 A1 | 5/2012 | Giesen et al. |
| 2013/0217748 A1 | 8/2013 | Sartingen et al. |

FOREIGN PATENT DOCUMENTS

| | | |
|---|---|---|
| CA | 2379682 | 1/2001 |
| CN | 101214050 | 7/2008 |
| CN | 111419755 | 7/2020 |
| EP | 1090630 | 4/2001 |
| EP | 1803800 | 7/2007 |
| EP | 2415459 | 2/2012 |
| FR | 2791564 | 10/2000 |
| JP | 2006342164 | 12/2006 |
| RU | 2494725 | 10/2013 |
| WO | 1997/025972 | 7/1997 |
| WO | 2013/010085 | 1/2013 |
| WO | 2013/092080 | 6/2013 |
| WO | 2015/131220 | 9/2015 |

OTHER PUBLICATIONS

Angele et al., 2002, "L-Arginine: A unique amino acid for improving depressed wound immune function following hemorrhage," European Surgical Research 34:53-60.
Anonymous, 2015, "Mezocomplex," World of Cosmetics.—Nov. 2015.—N 11 (214).—p. 2.
Cosmetics Info https://web.archive.org/web/20150703014433/https://cosmeticsinfo.org/sodium-lauryl-sulfate-and-sodium-laureth-sulfate, obtained from the internet Sep. 2, 2019, Internet Archive Wayback Machine date, Jul. 3, 2015.
GAD, 2010, "Anti-aging effects of L-arginine," Journal of Advanced Research 1:169-177.
International Search Report and Written Opinion of the International Searching Authority in International Application No. PCT/US2015/068279, mailed Mar. 31, 2016.
Kirk et al., 1993, "Arginine stimulates wound healing and immune function in elderly human beings," Surgery 114:155-160.
Kramer et al., 2013, "In vitro cell migration and invasion assays," Mutation Research 752:10-24.
Matilla et al., 2002, "La glicina: Un nutrient antioxidante protector celular," Nutr. Hosp. 17(1):2-9 [Spanish w/ English abstract].
Ramachandran, ed., 1967, "Chapter 1: Composition of collagen and allied proteins," Treatise on Collagen vol. 1: Chemistry of Collagen pp. 1-72.
Spier et al., 1956, "Zur analytischen und funktionellen Physiologie der Hautoberfläche," Hautarzt 7(2):55-60.

(Continued)

*Primary Examiner* — Rayna Rodriguez

(57) ABSTRACT

Described herein, are personal care compositions comprising taurine in combination with arginine and glycine, and methods for using the compositions to effect reduction of skin irritation and or inflammation, and/or improving barrier repair of the skin.

10 Claims, No Drawings

(56) References Cited

OTHER PUBLICATIONS

Szymanski et al., 2008, "Taurine and its potential therapeutic application," Postepy Hig Med Dosw 62:75-86 [Polish w/English abstract].
Wu et al., 2002, J Food and Drug Analysis 10(3):170-177.
Carver Korea, 2017, "Real Eye Cream for Face Special Night", Mintel Database GNPD AN: 4669499.
Cleo Lab, 2020, "Cica Peptide Cream", Mintel Database GNPD AN: 7916995.
Darl Kuhn, 2006, "Micronized Amino Substituted Hydroxyphenyl Benzophenone Derivatives ED", IP.com, 151 pages.
Holika Holika, 2020, "Cream in serum Gift Set", Mintel Database GNPD AN: 7254203.
International Search Report and the Written Opinion of the International Searching Authority issued in International Application PCT/US2022/043153 mailed Jan. 5, 2023.
Laboratoires Filorga, 2012, "Absolute Wrinkles Correction Cream", Mintel Database GNPD AN: 1871659.
Laboratoires Filorga, 2015, "Detox Body Treatment", Mintel Database GNPD AN: 3461757.
Laboratoires Filorga, 2018, "UV-Defence SPF 50+", Mintel Database GNPD AN: 5862827.
Murad, 2014, "Moisture Cream SPF 30 PA+++", Mintel Database GNPD AN: 2582329.
SM Life Science, 2019, "Eye Renewal Cream", Mintel Database GNPD AN: 6867437.

PERSONAL CARE COMPOSITION COMPRISING TAURINE, ARGININE, GLYCINE

BACKGROUND

Skin can be irritated or damaged as a result of various factors, e.g. climate, hydration level, etc. As, such there is a need for products which do not further irritate or damage the skin; and actually promote skin cell viability and/or skin barrier repair. Embodiments of the present invention are designed to meet these needs.

BRIEF SUMMARY

In some embodiments, the present invention provides a personal care composition comprising taurine, arginine and glycine. In other embodiments, the present disclosure provides a method for reducing skin irritation and/or inflammation; and/or improving barrier repair function of the skin, comprising applying an effective amount of a personal care composition comprising taurine, arginine and glycine to the skin of a subject in need thereof.

Further areas of applicability of the present disclosure will become apparent from the detailed description provided hereinafter. It should be understood that the detailed description and specific examples, while describing certain embodiments, are intended for purposes of illustration only and are not intended to limit the scope of the invention.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Taurine or 2-aminoethanesulfonic acid is an amino sulfonic acid which is present in most animal tissues. Taurine regulates intracellular $Ca^{2+}$ concentration, act as a neuromodulator, and is responsible for osmoregulation. Taurine has previously been used in various therapies and compositions. For example, nutritional supplements often include taurine.

L-Arginine is a basic naturally occurring amino acid which is known to be involved in several metabolic pathways within the human body. Arginine is present in natural moisturizing factor and collagen in measurable quantities. Collagen is the essential protein required to keep the connective tissue and skin flexible and firm. It serves as a precursor for the synthesis not only of proteins but also of urea, polyamines, proline, glutamate, creatine and agmatine.

Glycine is another important amino acid which helps to create muscle tissue and convert glucose into energy. Approximately one third of collagen is comprised of glycine. Glycine is also one of the amino acids which are the most abundant components of natural moisturizing factor.

It has been found in accordance with the present disclosure that the combination of taurine, arginine and glycine improves the barrier repair function of the skin and also reduces skin irritation and inflammation. Furthermore, it is unexpectedly been found that the effect of taurine is synergistically enhanced in the presence of arginine and glycine.

The present disclosure thus provides, in some embodiments, a personal care composition (Composition 1) comprising taurine, arginine and glycine, in a taurine:arginine:glycine weight ratio of (1.5-69):(0.5-40):(0.5-1.5); for example:

1.1. Composition 1, wherein the weight ratio of taurine:arginine:glycine in the composition is (2-69):(1-40):(0.5-1.5);
1.2. Composition 1, wherein the weight ratio of taurine:arginine:glycine in the composition is (2-15):(1-10):(0.5-1.5);
1.3. Composition 1, wherein the weight ratio of taurine:arginine:glycine in the composition is (2-13):(1-7):(0.75-1.25);
1.4. Composition 1, wherein the weight ratio of taurine:arginine:glycine in the composition is (2-13):(1-7):(0.9-1.1);
1.5. Composition 1, wherein the weight ratio of taurine:arginine:glycine in the composition is (2-13):(1-7):1;
1.6. Composition 1, wherein the weight ratio of taurine:arginine:glycine in the composition is (60-69):(25-35):(0.5-1.5);
1.7. Composition 1, wherein the weight ratio of taurine:arginine:glycine in the composition is (62-69):(28-35):(0.75-1.25);
1.8. Composition 1, wherein the weight ratio of taurine:arginine:glycine in the composition is (64-69):(30-35):(0.9-1.1);
1.9. Composition 1, wherein the weight ratio of taurine:arginine:glycine in the composition is (64-69):(30-35):1;
1.10. Composition 1, wherein the weight ratio of taurine:arginine:glycine in the composition is 65:34:1;
1.11. Composition 1, wherein the weight ratio of taurine:arginine:glycine in the composition is 69:30:1;
1.12. Any one of Compositions 1 to 1.11, wherein the combined total amount of taurine, arginine and glycine in the composition is from 0.001% to 5% of the composition by weight.
1.13. Any one of Compositions 1 to 1.12, wherein the combined total amount of taurine, arginine and glycine in the composition is from 0.01% to 5% of the composition by weight.
1.14. Any one of Compositions 1 to 1.13, wherein the combined total amount of taurine, arginine and glycine in the composition is from 0.01-3% of the composition by weight.
1.15. Any one of Compositions 1 to 1.14, wherein the combined total amount of taurine, arginine and glycine in the composition is from 0.1-3% of the composition by weight.
1.16. Any one of Compositions 1 to 1.15, wherein the combined total amount of taurine, arginine and glycine in the composition is from 0.5-3% of the composition by weight.
1.17. Any one of Compositions 1 to 1.16, wherein the combined total amount of taurine, arginine and glycine in the composition is from 1-3% of the composition by weight.
1.18. Any one of Compositions 1 to 1.17, wherein arginine is L-arginine.
1.19. Any one of Compositions 1 to 1.18, wherein the composition is selected from a rinse off composition and a leave-on composition.

1.20. Composition 1.19, wherein the rinse off system is selected from bar soap, shower gel, shampoo, conditioner, liquid soap, dish soap and facial wash; and the leave on composition is selected from hand lotion, body lotion, facial cream, diaper cream, sunscreen cream or lotion and underarm products.

1.21. Any one of Compositions 1 to 1.20, wherein the composition reduces skin irritation or improves barrier repair function of the skin.

1.22. Any one of Compositions 1 to 1.21, wherein the composition reduces skin irritation.

1.23. Any one of Compositions 1 to 1.22, wherein the composition improves barrier repair function of the skin.

1.24. Any one of Compositions 1 to 1.23, wherein the composition further comprises a carrier comprising a personal care ingredient.

1.25. Composition 1.24, wherein the personal care ingredient is selected from a fragrance, a preservative, a solvent, a propellant, an exfoliant, a surfactant such as sodium dodecyl sulfate, a skin cell renewal agent, an anti-acne drug, an antiperspirant compound, an insect repellent chemical, a sunscreen agent, a decomposition product of an oil or a fat, and a mixture of two or more thereof.

1.26. Composition 1.24 or 1.25, wherein the personal care ingredient is an exfoliant.

1.27. Composition 1.24 or 1.25, wherein the personal care ingredient is a surfactant.

1.28. Any one of Compositions 1 to 1.27, wherein the surfactant is sodium dodecyl sulfate.

1.29. Any one of Compositions 1 to 1.28, wherein the composition further comprises an additional agent for improving barrier function of the skin.

1.30. Any one of Compositions 1 to 1.29, wherein the additional agent for improving barrier function of the skin is selected from the group consisting of glycerin, vitamin $B_3$, a natural moisturizing factor such as a ceramide, hyaluronic acid, cholesterol, a fatty acid, a triglyceride, a phospholipid, a glycosphingolipid, urea, linoleic acid, a glycosaminoglycan, a mucopolysaccharide and a mixture of two or more thereof.

In further embodiments, the present invention provides a method for reducing skin irritation and/or inflammation; or improving barrier repair of the skin comprising applying to skin an effective amount of a formulation according to any one of Compositions 1 to 1.30.

In other embodiments, the present invention provides a method for reducing skin irritation and/or inflammation of a personal care composition, comprising formulating the personal care composition to include taurine, arginine and glycine, in a taurine:arginine:glycine weight ratio according to any one of Compositions 1 to 1.30.

Still further embodiments provide a method for improving the ability of a personal care composition to effect barrier repair of the skin, comprising formulating the personal care composition to include taurine, arginine and glycine, in a taurine:arginine:glycine weight ratio according to any of Compositions 1 to 1.11.

In other embodiments, the present invention provides the use of a combination of taurine, arginine and glycine, in a taurine:arginine:glycine weight ratio of 65:34:1 for the preparation of a personal care composition.

In some embodiments, the disclosure provides a personal care composition comprising taurine, arginine and glycine, wherein taurine is in free or physiologically acceptable salt form. The term taurine also encompasses derivatives of taurine such as its salts and esters as well as its complexes, conjugates and the like, and specifically includes biogenic taurine derivatives such as chloramine/taurine complexes, as well as synthetic and semi-synthetic derivatives. Unless otherwise specified, weight ratios of taurine described herein are based on the neutral form of taurine having molecular formula $C_2H_7NSO_3$.

Arginine and glycine can each be in free or physiologically acceptable salt form. Arginine is preferably L-arginine. Unless otherwise specified, weight ratios of arginine and glycine described herein are based on their neutral forms having molecular formula of $C_6H_{14}N_4O_2$, and $C_2H_5NO_2$, respectively.

The compositions of the present disclosure include health care products such as skin care products, underarm products and hair care products, and include both rinse off compositions and leave-on compositions. Rinse off products include but are not limited to bar soap, body wash, shower gel, shampoo, conditioner, liquid hand or other soap, dish soap and facial wash; and leave on compositions include lotions, including but not limited to hand lotion and body lotion, creams including but not limited to facial cream, diaper cream and sunscreen cream, and underarm products including but not limited to antiperspirant sticks, gels, roll-on and pump sprays.

In some embodiments, the compositions of the present do not include dihydroquercetin or a derivative thereof. In some such embodiments, the compositions are hair care compositions. In some embodiments, the compositions do not contain any free (i.e., not incorporated into protein) amino acids other than taurine, arginine and glycine.

The compositions of the present disclosure can comprise a carrier. Suitable carriers for use with the compositions of the invention are well known in the art. The carrier can be a liquid, semi-solid or solid. Carriers among those useful herein include liquids, pastes, ointments, and gels, and can be transparent, translucent or opaque. The carrier may comprise any of a variety of materials, including emulsifiers, thickeners, fillers, and preservatives.

In some embodiments, the combination of taurine, arginine and glycine can be present in the composition in an amount effective to reduce the skin irritation and inflammation, or improve barrier repair function of the skin. Typically, the combined amount of taurine, arginine and glycine present in the composition will be from 0.001% to 5% by weight; for example from 0.01% to 5% by weight; for example from 0.01-3% by weight; for example from 0.1-3% by weight; for example from 0.5-3% by weight; for example from 1-3% by weight. It should be understood that the amount of combined amino acid incorporated in the composition may be varied depending on the type of the composition, the contents of the composition, the purpose of the use and so on. For example, for most rinse off compositions, the combined amount of taurine, arginine and glycine present in the composition will be from 0.01% to 5% by weight, while for most leave on compositions, the combined amount of taurine, arginine and glycine present in the composition will be from 0.001% to 5% by weight. Thus, for example, rinse off compositions such as, for example, shower gel compositions, bar soap compositions, shampoos, conditioners, liquid soaps, dish liquids and facial washes can include taurine, arginine and glycine in a combined amount of 0.001-5%, 0.01-3%, 0.1-3%, 0.5-3%, or 1-3%, or 1%, 1.5%, 2%, 2.5%, 3%, 3.5%, 4%, 4.5% or 5% by weight relative to the total weight of the composition. Leave on compositions such as, for example, hand or body lotions, facial creams, diaper creams and the like can include taurine, arginine and glycine in a combined amount of 0.001 to 5%, 0.01 to 5%, 0.01-3%, 0.1-3%, 0.5-3%, 1-3%, or 1%, 1.5%, 2%, 2.5%, 3%, 3.5%, 4%, 4.5% or 5% by weight relative to the total weight of the composition.

The weight ratio of taurine:arginine:glycine incorporated in the compositions of the present disclosure is typically from (1.5-69):(0.5-40):(0.5-1.5), or from (2-69):(1-40):(0.5-1.5), respectively. In some embodiments, the ratio of taurine:arginine:glycine incorporated in the compositions of the present disclosure is from (2-15):(1-10):(0.5-1.5); or from (2-13):(1-7):(0.75-1.25); or from 2-13):(1-7):(0.9-1.1); or from (2-13):(1-7):1.

In other embodiments, the ratio of taurine:arginine:glycine incorporated in the compositions of the present disclosure is from (60-69):(25-35):(0.5-1.5); or from (62-69):(28-35):(0.75-1.25); or from (64-69):(30-35):(0.9-1.1); or from (64-69):(30-35):1, respectively. In some preferred embodiments, the ratio of taurine:arginine:glycine incorporated into the compositions of the present disclosure is from 65:34:1, respectively. In some embodiments, the ratio of taurine:arginine:glycine incorporated in the compositions of the present disclosure is from 69:30:1, respectively.

In some embodiments, compositions of the disclosure confer one or more benefits in addition to those conferred by the actives in the composition. These include reducing skin irritation and/or inflammation; and/or improving barrier repair function. In some embodiments, the skin irritation or inflammation that is reduced by the combination of taurine, arginine and glycine in accordance with the present disclosure may be caused by various factors, e.g. sun exposure, other topical compositions, climate, dehydration, etc.

In some embodiments, the compositions of the present invention are effective to, inter alia, reduce skin irritation and/or inflammation; and/or improve barrier repair function consequent to any known irritant or compound that is potentially irritating, especially to sensitive skin. Irritation may also be caused by elements which indirectly cause the skin to become more sensitive to other chemicals or environmental conditions which would not normally cause irritation.

In some embodiments, the compositions of the present invention can further include one or more additional agents that reduce skin irritation or improve barrier repair of the skin. The compositions of the present invention can be used to enhance the effects of such agents known to reduce skin irritation or improve barrier repair of the skin. The additional agent may be any agent which is known to reduce skin irritation or improve barrier repair of the skin in the art, and includes, for example and not limitation, camphor and trans-4-tert-butyl cyclohexanol; agents for improving barrier repair of the skin such as glycerin, vitamin B$_3$, natural moisturizing factors such as ceramides, hyaluronic acid, cholesterol, fatty acids, triglycerides, phospholipids, glycosphingolipids, urea, linoleic acid, glycosaminoglycans and mucopolysaccharide.

The compositions of the present invention can be manufactured according to conventional methods known to those skilled in the art. In some embodiments the compositions of the present invention are prepared by admixing taurine, arginine and glycine in a particular weight ratio, and formulating the combination in a carrier that comprises ingredients that are suitable for use in a personal care product.

The present invention is further illustrated through the following non-limiting examples.

EXAMPLES

Example 1

To determine barrier repair function of taurine combined with L-arginine and glycine, in vitro experiments are conducted using HaCaT cells. HaCaT cells are spontaneously transformed aneuploid immortal keratinocyte cell line from adult human skin and are grown until 100% confluent. After that, each well is scratched with 1000 μl tip to create the gap and washed with 1 ml of PBS twice to eliminate dead floating cells. Following that, cells are treated with 1 ml of culture media for control (untreated), Taurine (0.0005% by weight), and amino acid complex of taurine (0.0005% by weight) combined with L-arginine (0.0001% by weight) and glycine (0.0001% by weight). Then, initial measurements of gap distance are taken using microscope (OLYMPUS IX71). Next, the treated cells are incubated for 24 hours and measurements are taken again. The results are shown in Table 1 (below).

TABLE 1

| Treatment | Cell migration in 24hr (% of control) |
| --- | --- |
| Untreated | 5 |
| taurine (0.0005%) | 66 |
| taurine (0.0005%) + L-arginine (0.0001%) + glycine (0.0001%) | 77 |

The migration assay measures cell migration in order to evaluate the barrier repair. The smaller the gap, the greater migration rate, which suggests better barrier repair function. Treatment of cells for 24 hours with taurine enhanced migration compared to untreated cells (5% vs. 66%). The effect of taurine is enhanced in the presence of arginine and lysine (66% vs 77%). The data described in Table 1 (above) demonstrates that taurine in combination with arginine and glycine synergistically improves barrier repair function.

Example 2

To measure skin irritation, in vitro experiments are conducted using 3D EpiDerm skin models (SIT 200 skin irritation model, MatTek Corporation, Ashland, MA 01721). The irritation assay measures IL-la protein released by the cells to the media to evaluate the level of skin irritation and inflammation. In vitro skin samples are treated topically with 30 μl of test compounds (taurine (1% by weight) or taurine-L-arginine-glycine complex (1% by weight) of 2:1:1 (a mixture of 0.5% taurine, 0.25% L-arginine and 0.25% glycine, by weight) for 1 hour in tissue culture incubator. To induce irritation, cells are co-treated with 0.05% SDS and the test compounds. Following the incubation, skin samples are washed with PBS and placed in a culture medium and incubated for 24 hours. Cell culture media are collected for IL-la release assay. IL-la release is analyzed by ELISA assay kit (R&D Systems, Minneapolis, MN 55413). The results are shown in Table 2 (below).

TABLE 2

| Treatment | IL-1α release (% of control) |
| --- | --- |
| Untreated | 100 |
| 0.05% SDS | 120 |
| 0.05% SDS, 1% taurine | 70 |
| 0.05% SDS, 1% taurine-L-arginine-glycine complex | 42 |

The greater IL-1α release, the greater the irritation potential. Treatment with 0.05% SDS increased IL-1α release by 20 percent. Table 2 (above) shows that MatTek tissue treated with 1% taurine-L-arginine-glycine complex released a significantly lower amount of IL-1α compared to taurine alone (70% vs 42%). It can be concluded that the irritation/inflammation is synergistically reduced after treatment with taurine combined with arginine and glycine.

Example 3

Taurine-L-arginine-glycine complexes with various ratios of taurine:L-arginine:glycine are further tested in an in vitro migration assay and an irritation assay. The ratios of taurine:L-arginine:glycine by weight tested in this experiment are shown in Table 3 (below).

TABLE 3

| Taurine-L-arginine-glycine complex Sample | Taurine:arginine:glycine ratio (by weight) |
| --- | --- |
| 1 | 2:1:1 |
| 2 | 6:3:1 |
| 3 | 6:3.5:0.5 |
| 4 | 6.5:3:0.5 |
| 5 | 6.5:3.4:0.1 |
| 6 | 6.9:3:0.1 |

The in vitro migration assay is conducted generally as described above. However, in this experiment, cells are treated with 0.001 wt. % of Taurine-L-arginine-glycine complexes. Cell migration is measured at 24 hours and 48 hours. The results are shown in Table 4 (below).

TABLE 4

| Treatment | Cell migration in 24 hr (% of control) | Cell migration in 48 hr (% of control) |
| --- | --- | --- |
| untreated | 3 | 3 |
| 1 (0.001%) | 99 | 43 |
| 2 (0.001%) | 151 | 112 |
| 3 (0.001%) | 124 | 75 |
| 4 (0.001%) | 149 | 89 |
| 5 (0.001%) | 188 | 144 |
| 6 (0.001%) | 165 | 113 |

Example 4

Samples 1-6 are evaluated in the in vitro irritation assay as described above in Example 2. The results are shown in Table 5 (below).

TABLE 5

| Treatment | IL-1α release (% of control) |
| --- | --- |
| Untreated | 100 |
| 0.05% SDS | 140 |
| 0.05% SDS/1% taurine | 114 |
| 0.05% SDS/1% AA1 | 102 |
| 0.05% SDS/1% AA2 | 101 |
| 0.05% SDS/1% AA3 | 103 |
| 0.05% SDS/1% AA4 | 106 |
| 0.05% SDS/1% AA5 | 98 |
| 0.05% SDS/1% AA6 | 102 |

These results demonstrate that taurine in combination with arginine and glycine synergistically improves barrier repair function and also synergistically reduces the skin irritation and inflammation.

What is claimed is:

1. A method for improving barrier repair function of the skin, wherein the method comprises applying an effective amount of a personal care composition on the skin of a subject in need thereof;
    wherein the personal care composition comprises taurine, arginine and glycine; and
    wherein the taurine, arginine, and glycine are in a weight ratio of (60-69):(25-35):(0.5-1.5);
    wherein the effective amount of the personal care composition comprises a combined amount of taurine, arginine, and glycine present in the composition of from 0.001% to 5% by weight; and
    wherein the personal care composition does not contain any free amino acids other than taurine, arginine, and glycine.

2. The method according to claim 1, wherein the personal care composition further comprises at least one additional agent selected from the group consisting of camphor, trans-4-tert-butyl cyclohexanol, glycerin, vitamin B3, ceramides, hyaluronic acid, cholesterol, fatty acids, triglycerides, phospholipids, glycosphingolipids, urea, linoleic acid, glycosaminoglycans and mucopolysaccharide.

3. The method according to claim 1, wherein the total amount of taurine, arginine and glycine in the personal composition is from 0.001% to 1% by weight.

4. The method according to claim 3, wherein the total amount of taurine, arginine and glycine in the personal composition is 0.001% by weight.

5. The method according to claim 3, wherein the total amount of taurine, arginine and glycine in the personal composition is 1% by weight.

6. The method according to claim 1, wherein arginine is L-arginine.

7. The method of claim 1, wherein the effective amount of the personal care composition comprises a combined amount of taurine, arginine, and glycine present in the composition of from 0.01% to 5% by weight, or from 0.01% to 3% by weight, or from 0.1% to 3% by weight, or from 0.5% to 3% by weight, or from 1%-3% by weight of the composition.

8. The method of claim 1, wherein the personal care composition further comprises a carrier, the carrier comprising emulsifiers, thickeners, fillers, and preservatives.

9. The method of claim 1, wherein the personal care composition is a rinse off composition, wherein the rinse off composition is selected from the group consisting of a bar soap, a body wash, a shower gel, a shampoo, a conditioner, a liquid hand soap, and a facial wash.

10. The method of claim 1, wherein the personal care composition is a leave-on composition, wherein the leave-on composition is selected from the group consisting of a hand lotion, a body lotion, a facial cream, a diaper cream, a sunscreen cream, and underarm products.

* * * * *